United States Patent
Loeb

(10) Patent No.: US 6,635,052 B2
(45) Date of Patent: Oct. 21, 2003

(54) MULTI-FIBER LASER DEVICE FOR SHRINKING TISSUE

(75) Inventor: Marvin P. Loeb, Huntington Beach, CA (US)

(73) Assignee: Trimedyne, Inc., Irvine, CA (US)

( * ) Notice: Subject to any disclaimer, the term of this patent is extended or adjusted under 35 U.S.C. 154(b) by 27 days.

(21) Appl. No.: 09/832,639

(22) Filed: Apr. 11, 2001

(65) Prior Publication Data

US 2002/0151879 A1 Oct. 17, 2002

(51) Int. Cl.[7] .............................................. A61B 18/20
(52) U.S. Cl. ............................... 606/15; 606/13; 606/17
(58) Field of Search ............................ 606/3, 8, 10–17, 606/27, 28

(56) References Cited

U.S. PATENT DOCUMENTS

| | | | | | |
|---|---|---|---|---|---|
| 4,448,188 A | * | 5/1984 | Loeb | .............................. | 606/7 |
| 4,799,479 A | * | 1/1989 | Spears | ........................... | 606/7 |

FOREIGN PATENT DOCUMENTS

| | | | | |
|---|---|---|---|---|
| WO | 9210142 | * | 6/1992 | ................... 606/15 |

* cited by examiner

Primary Examiner—David M. Shay
(74) Attorney, Agent, or Firm—Olson & Hierl, Ltd.

(57) ABSTRACT

Light energy is utilized to shrink or tighten tissue surrounding a hollow organ, cavity, duct or naturally occurring or surgically created passage by cross-linking the collagen of the surrounding tissue and ccausing scar formation therein. The present device may be used in the esophagus in the area of the sphincter to treat GERD, in the female urethra to treat FSI or at the vesicouretal junction to treat VUR.

In the present device, a plurality of plastic tubes, each containing a slidable optical fiber with a sharpened distal end, are affixed to the outer surface of a balloon, which is mounted near the distal end of a closed end catheter. The balloon catheter may be inserted into the body inside a retractable protective sheath. When the sheath is retracted, exposing the balloon, the balloon is inflated, which presses the distal ends of the plastic tubes against the surrounding tissue. The optical fibers are simultaneously advanced manually a selected distance out of the plastic tubes into the tissue surrounding the organ, cavity, duct or passage, reducing the diameter thereof.

In a preferred embodiment, superelastic metal tubes with sharp, syringe-shaped ends, which have been preformed into a curved shape, are attached to the distal ends of the optical fibers. When advanced and released from the confines of the plastic tubes, the metal tubes revert to their original shape and curve outward, piercing the tissue. A fluid pathway is provided for injecting a bulking material, such as a biocompatible collagen, to further reduce the diameter of the passageway. The injected collagen can be cross-linked by laser energy, thereby reducing the mobility of the injected bulking material.

9 Claims, 7 Drawing Sheets

MULTI-FIBER LASER DEVICE FOR SHRINKING TISSUE

FIELD OF THE INVENTION

The invention relates to devices and methods for shrinking collagen in body tissue.

BACKGROUND OF THE INVENTION

Gastro esophageal reflux disease or "GERD", female stress incontinence or "FSI" and vesicouretal reflux or "VUR" affect millions of people in the United States and many more overseas. Pharmaceuticals, such as omeprazole, marketed as Prilosec® by AstraMerck of Wayne, Pa., or rabeprazole sodium, marketed as Aciphex® by Esai Co. of Titusville, N.J. are able to palliate but not cure GERD and usually must be taken for the rest of the person's lifetime. Surgical treatment of GERD, a procedure called Nissen Fundoplication, is highly invasive, requires general anesthesia, a costly hospital stay and extensive recuperation and creates significant adverse effects, including infections and persistent pain. Likewise, surgical treatments for FSI, including slings, staples, screws and other devices, as well as the injection of collagen, such as manufactured by the Collagen Corporation and distributed as Contigen® by C. R. Bard, Inc. of Murray Hill, N.J., are invasive, entail substantial cost and frequently do not provide lasting relief.

It would be desirable to be able to treat GERD, VUR, FSI and other conditions in a minimally invasive, non-surgical procedure that could be rendered in a few minutes in a hospital outpatient department or outpatient surgical center, as well as in a physician's office, without general anesthesia, at modest cost and with little recuperation time.

SUMMARY OF THE INVENTION

Collagen present in tissue surrounding a hollow organ, body cavity, duct or naturally occurring or surgically created passage can be treated with a device embodying the present invention to tighten the tissue around the hollow organ, cavity, duct or passage, such as the esophagus in the area of the sphincter or the female urethra near the bladder neck, so as to alleviate conditions such as gastro-esophageal reflux disease, female stress incontinence, vesico-uretal reflux, and the like. A balloon made of a biocompatible, flexible (non-compliant) or elastic (compliant) material is joined to the distal end of a flexible catheter provided with a rounded, atraumatic, closed distal end. The proximal end of the catheter is provided with a handpiece for manipulating the catheter. One or more ports in the catheter, and within the balloon, provide fluid communication from the catheter into the balloon. A fluid inflow tube joined to the catheter in or near the distal end of the handpiece, provides a passageway for a fluid to be infused through the fluid inflow tube into the catheter to inflate the balloon. An optional vent valve in or near the distal end of the handpiece, permits air to escape when fluid is infused into the catheter to inflate the balloon.

A plurality of small, flexible tubes are situated on the exterior of the balloon. The tubes terminate preferably at about the balloon's largest outside diameter when expanded. The proximal ends of the tubes pass through the wall of the catheter and open into its inner lumen, creating a channel for fluid flow therethrough. The openings in the catheter through which the tubes extend are sealed with an adhesive or thermal bonding. The distal end portions of the tubes are free, i.e., not attached to the external surface of the balloon.

An optical fiber is slidably disposed within each of the tubes. The distal ends of the optical fibers can be beveled or sharpened if desired to facilitate penetration into tissue. The optical fibers extending from the proximal ends of the tubes are joined into a bundle within the catheter by enclosing the same in a casing, for example, made of a heat shrinkable film, or in a sleeve made of a flexible plastic material, as known in the art. The bundle of optical fibers extends through the handpiece, and can be connected to a source of high intensity light or coherent light such as a laser.

A slidable control button, which may be engaged by the operator's thumb, is disposed within a slide channel on the exterior of the handpiece. The portion of the button which extends through the slide is attached to a metal sleeve which, in turn, is attached to and surrounds the bundle of optical fibers. When the button is advanced a predetermined distance, an audible "click" is created by a ratchet mechanism, and the optical fibers are extended a like distance out of the distal ends of the tubes in which they are disposed.

The above described device is slidably disposed within a flexible, retractable, protective sheath, which has markings at predetermined intervals from its distal end. The catheter itself also has markings at the same intervals beginning at the proximal end of the sheath. In use, the catheter/balloon/tube assembly, contained within the sheath, may be inserted into a hollow organ, duct, cavity or passage to a selected position, which has been earlier determined in any convenient manner.

When placed, the protective sheath is retracted a distance sufficient to expose all or a desired portion of the balloon. A biocompatible fluid is then infused to inflate the balloon, which urges the distal ends of the tubes up against the inner surface of the hollow organ, cavity, duct or passage to be treated. Since the distal end portions of the tubes are not affixed to the balloon, they extend away from the balloon at a greater angle than if they were fully affixed to the balloon.

The optical fibers are introduced into the tissue a desired distance by the operator's thumb advancing the control button a like distance. For example, in the treatment of GERD or FSI, the device would be positioned in the esophagus at or near the level of the sphincter or in the female urethra proximal to the bladder neck, respectively. To avoid thermal damage to the sensitive inner lining (mucosa) of the esophagus or urethra, light energy is not transmitted through the optical fibers until they have been inserted through the mucosa into the tissue. Light energy is then emitted for a time sufficient to shrink the tissue, causing mechanical cross linkage of collagen and internal scarring of the tissue. The result of this treatment a is tightening of the muscle tissue surrounding the sphincter or the urethra.

When light energy of a desired wavelength has been emitted at a desired level and for a sufficient amount of time, the fibers are retracted, the balloon is deflated, the protective sheath is advanced over the catheter/balloon/tube assemblage and the device is removed.

DESCRIPTION OF THE PREFERRED EMBODIMENTS

Figure 1A:
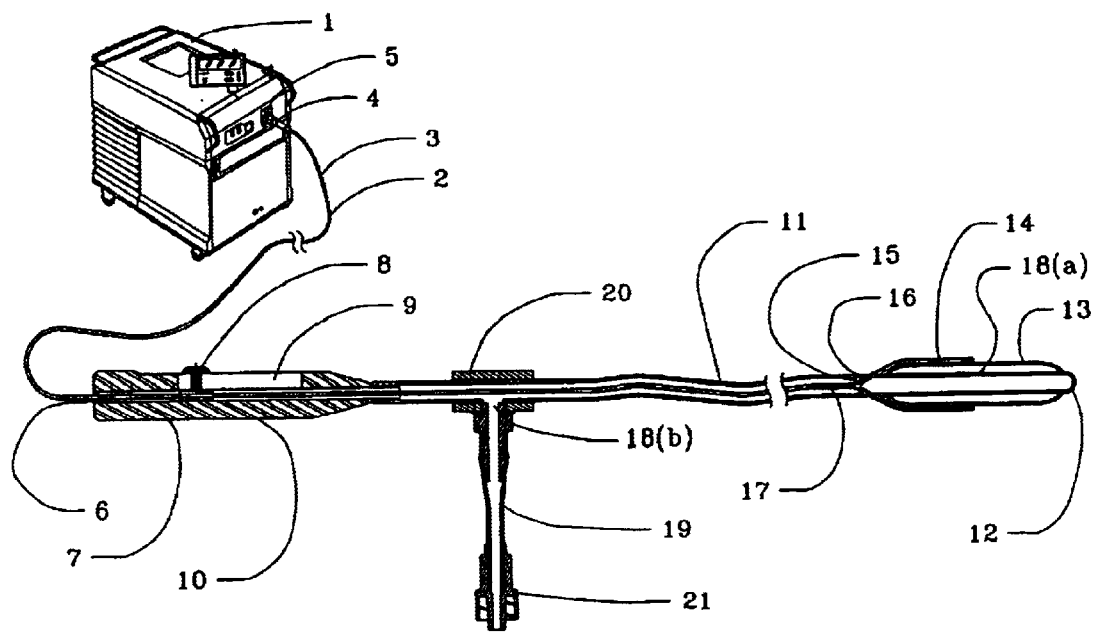
FIG. 1(a) is a schematic of the system and an enlarged, cross sectional side view of the handpiece/catheter/balloon/tube assembly of the device of the present invention, with the balloon deflated and without the protective sheath.

While this invention is susceptible of embodiment in many different forms, there is shown in the drawings and will be described herein in detail specific embodiments thereof, with the understanding that the present disclosure is to be considered as an exemplification of the principles of the invention and is not to be limited to the specific embodiments illustrated.

As shown in FIG. 1(a), a source of light energy 1, such as a laser or high intensity light source, is optically coupled to a plurality of optical fibers formed into a bundle 2 by encasing the optical fibers within a flexible plastic casing 3, such as a heat shrinkable film made, for example, of a fluorocarbon such as polytetrafluoroethylene, or a plastic tube made, for example, of polyethylene, polypropylene, polyurethane or like materials. Proper optical alignment is effected by attaching the connector 4 of bundle 2 to the optical coupler 5 of light source 1.

Optical fiber bundle 2 extends through channel 6 in handpiece 7 and is moveable therein. Control button 8 is moveably disposed within slide 9 in handpiece 7, and may be extended and retracted by thumb pressure of the operator (not shown). Control button 8 extends through slide 9 and is attached to metal sleeve 10, which is affixed to the exterior of fiber bundle 2 by an adhesive or similar expedient. A ratchet mechanism that emits an audible "click" each time control button 8 is advanced a given distance, for example, one millimeter, can be provided, if desired.

The proximal end of flexible catheter 11 is attached to the distal end of handpiece 7 in any convenient manner. The distal end 12 of catheter 11 is closed and formed into an atraumatic shape, e.g., a rounded or blunt shape.

A balloon 13, which may be made of a flexible, non-compliant plastic film, for example, such as polyurethane or polyethylene, or an elastic, compliant material, for example, such as latex or silicone, is disposed over or about the distal end portion of catheter 11, spaced from its distal end 12.

A plurality of plastic tubes 14, are attached, e.g., by an adhesive, thermal bonding or other means, to the exterior of balloon 13, at points just proximal to the distal end portions of the tubes, such that the distal end portions of tubes 14 are free (i.e., are not attached to the balloon). The tubes terminate at or just proximal to the mid-line of balloon 13. The proximal ends 15 of tubes 14 extend through the wall of catheter 11 and terminate within the lumen of catheter 11. The openings in catheter 11 through which tubes 14 extend are sealed with an adhesive or other fluid tight material 16. The free distal end portions of tubes 14 are about 2 to about 10 millimeters long, preferably about 4 to about 7 millimeters long.

Casing 3, surrounds optical fiber bundle 2, and terminates within catheter 11, usually about 5 to 30 millimeters proximal to the proximal ends 15 of tubes 14. Individual optical fibers 17 extend distally from casing 3 into tubes 14. When fully retracted by moving control button 8 on handpiece 7 to its rearward most position, the distal ends of optical fibers 17 extend up to but not beyond the distal ends of tubes 14. When control button 8 is advanced a predetermined distance, optical fibers 17 exit the distal ends of tubes 14 and extend outwardly the same distance. The distal ends of optical fibers 17 can be beveled or ground into a sharp point to facilitate their penetration into tissue. Optical fibers 17 usually are made of quartz or fused silica, and can have a core diameter of about 100 to 600 microns, preferably about 200 to 400 microns.

Ports 18(a) in the wall of catheter 11, within the confines of balloon 13, provide for entry of fluid to inflate balloon 13. Fluid infusion tube 19 is attached to catheter 11 through port 18(b), e.g., by an adhesive, thermal bonding or other means, in or distal to the distal end of handpiece 7. Fluid infusion tube 19 terminates in luer lock 21, which permits a source of liquid, such as distilled water, saline or a biocompatible, radio-opaque liquid, or a gas, such as carbon dioxide or air, to be injected into catheter 11 from a syringe or pump (not shown), which may be removably attached to luer lock 21. Optionally, a one-way vent valve (not shown), may be incorporated in catheter 11 through fitting 20 to enable air to escape when fluid is infused into catheter 11 to inflate balloon 13.

Luer lock 21, fluid tube 19, port 18(b), catheter 11 and port 18(a) create a fluid channel to inflate balloon 13. Since the open, proximal ends 15 of tubes 14 extend into the lumen of catheter 11, when fluid is injected into catheter 11 to inflate balloon 13, fluid also passes through the space between the optical fibers 17 and the lumens of tubes 14 and exits the distal ends of tubes 14 to cool the tissue surrounding balloon 13 at the point of penetration of optical fibers 17.

After balloon 13 has been inflated, optical fibers 17 may be extended a desired distance, about 2 to 20 mm, preferably about 3 to 15 mm, into the tissue in contact with balloon 13. When laser or high intensity light energy is transmitted through and emitted from the distal ends of optical fibers 17 into the tissue, shrinkage of collagen and scar formation takes place within the tissue surrounding balloon 13, tightening the tissue about the lumen of the hollow organ, cavity duct or passage. Unlike wires used to transmit RF or electrical energy, optical fibers are poor conductors of heat. Consequently, heat does not travel backward through the fibers to injure the sensitive mucosa of the organ, cavity, duct or passage. However, some heat may be conducted through the tissue, which could damage the mucosa or their underlying tissue. The emission of fluid from the distal ends of tubes 14 cools the mucosa or inner surface of the organ, cavity, duct or passage, preventing harm from conduction of heat thereto.

Figure 1B:
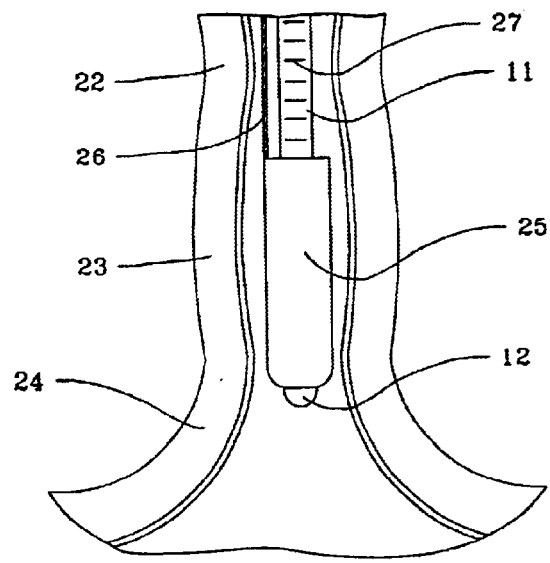
FIG. 1(b) is an external view of the distal end portion of the device of the present invention, which has been positioned in the esophagus in the area of the sphincter above the stomach, with the protective sheath in place.

As shown in FIG. 1(b), the distal end portion of the device of FIG. 1(a) has been inserted into the esophagus 22 and positioned in the area of the sphincter 23, above the stomach 24. Protective sheath 25 is disposed about the distal end portion of catheter 11, whose distal tip 12 is seen just distal to the distal end of sheath 22. A flexible plastic or metal rod 26, whose distal end is secured to the proximal end of protective sheath 25, extends through the esophagus 22, the oral cavity (not shown) and outside the patient's body. Markings 27 on the exterior of the distal end portion of catheter 11 enable the operator to view through an endoscope (not shown) how far sheath 25 has been retracted.

Figure 1C:
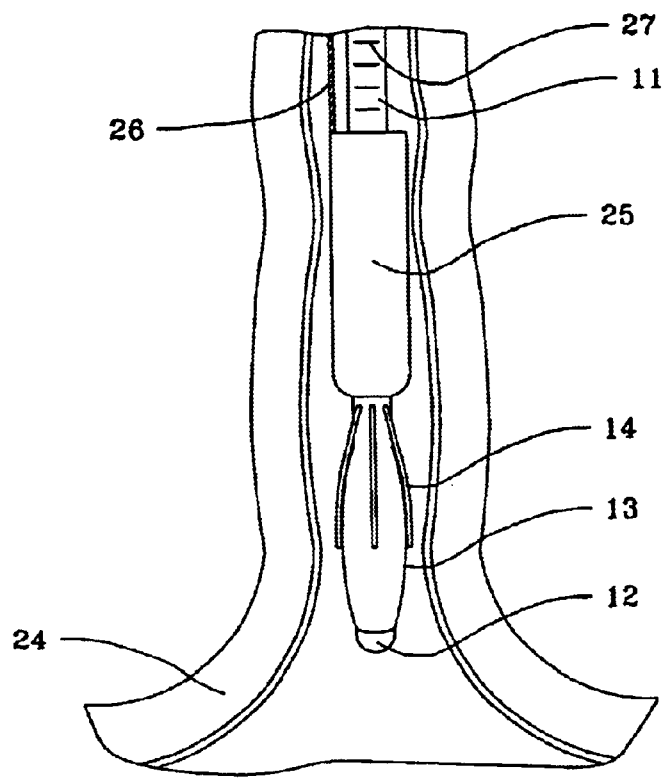
FIG. 1(c) is an external view of the device of FIG. 1(b) with the protective sheath retracted.

As seen in FIG. 1(c), by retracting rod 26, protective sheath 25 is moved rearwardly, exposing the distal end portion of catheter 11, balloon 13 and tubes 14.

Figure 1D:
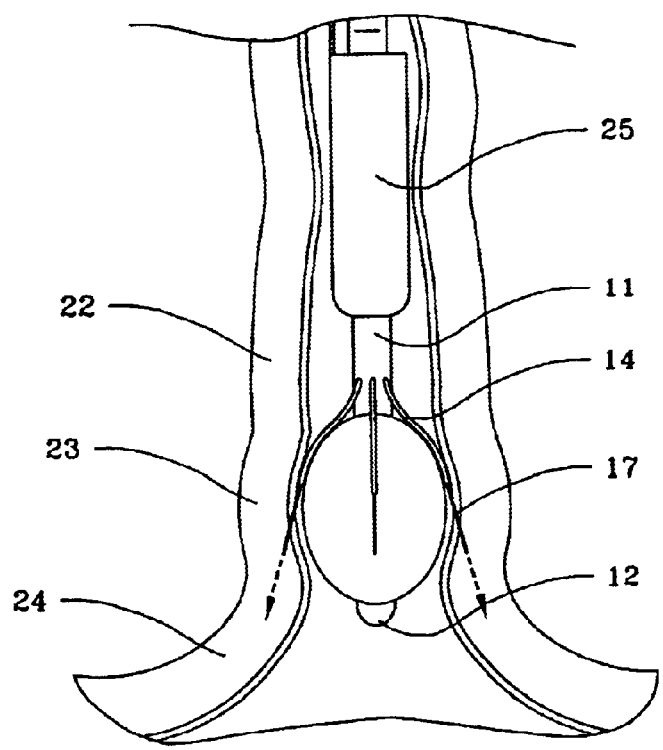
FIG. 1(d) is an external view of the device of FIG. 1(c) with the balloon inflated and the optical fibers extended into the tissue surrounding the esophagus.

FIG. 1(d) illustrates the device of FIG. 1(a), in which balloon 13 has been inflated, pressing tubes 14 against the inner surface of the esophagus 22 in the area of sphincter 23, above the stomach 24, with optical fibers 17 advanced out of tubes 14 into the surrounding tissue. The arrows indicate the direction of emission of laser energy. Balloon 13 may be made of a non-compliant plastic film, such as polyethylene or polyurethane, or an elastic, compliant material such as silicone or latex.

Figure 2:
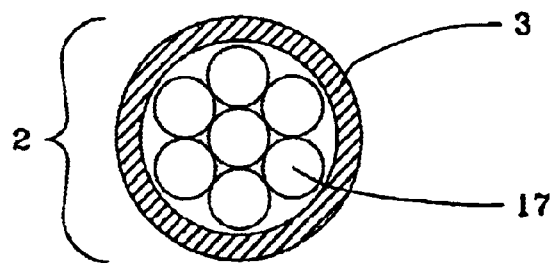
FIG. 2 is a cross sectional end view of the optical fiber bundle which extends from a source of light energy.

As shown in FIG. 2, bundle 2 of seven optical fibers 17 is encased in casing 3, which in this instance is a heat shrinkable film, such as polyethylene terphthalate or polytetrafluoroethylene. Casing 3 may also be a sleeve made of any other flexible plastic material, as known in the art. The number of optical fibers contained in the bundle can vary from 1 to 20, preferably from 1 to 10.

Figure 3:
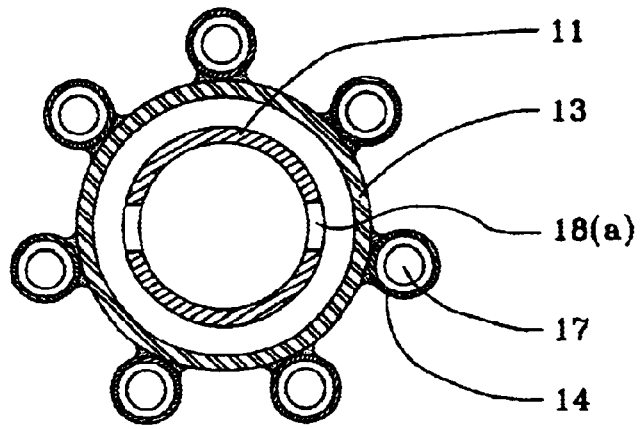
FIG. 3 is a cross sectional, end view of the catheter/balloon/tube/fiber assembly with the balloon deflated.

FIG. 3 shows a cross section of the catheter/balloon/tube/ fiber assembly, proximal to the mid-line of balloon 13, which is shown deflated. In this embodiment, six tubes 14, each containing an optical fiber 17, are evenly spaced about the exterior of balloon 13. Any number of tubes 14 may be used.

Figure 4:
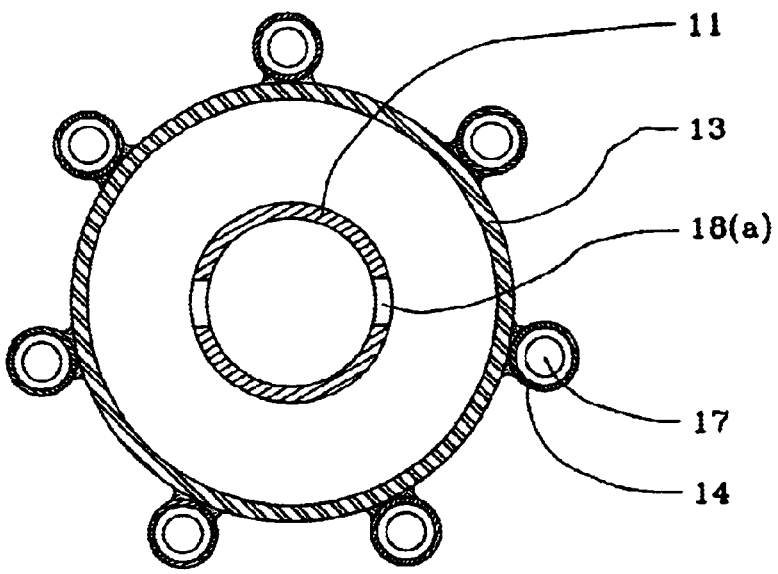
FIG. 4 is a cross sectional, end view of the assembly of FIG. 3 with the balloon inflated.

FIG. 4 illustrates the device of FIG. 3, with balloon 13 having been inflated by the infusion of fluid through ports 18(a). In this embodiment, the entire distal end portions of tubes 14 are affixed to balloon 13.

Figure 5:
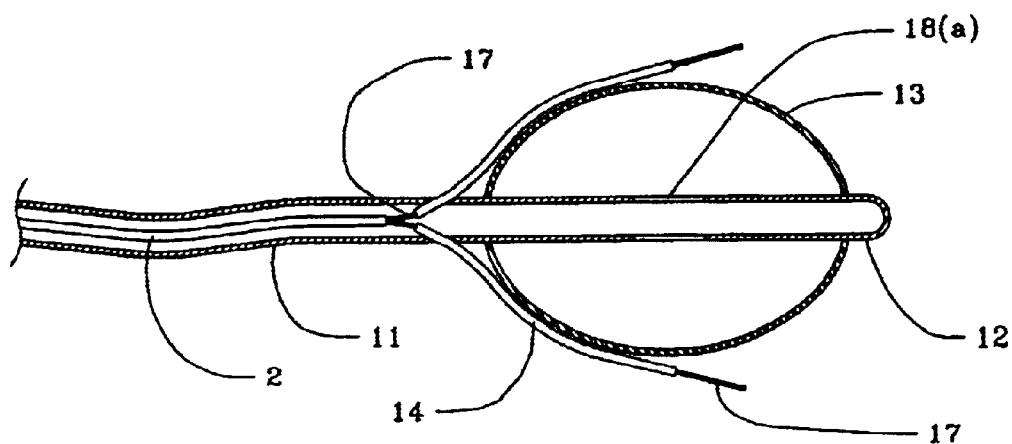
FIG. 5 is a partial, expanded, cross-sectional, side view of the preferred embodiment of the catheter/balloon/tube/fiber assembly with the balloon inflated.

An alternative embodiment of the device of FIG. 1(a) is seen in FIG. 5. In this embodiment, the distal end portions of tubes 14 are not affixed to balloon 13 and, when balloon 13 is inflated, tubes 14 extend from balloon 13 at an angle from the axis of catheter 11 greater than tubes 14 shown in FIG. 4, which are entirely affixed to balloon 13.

Figure 6:
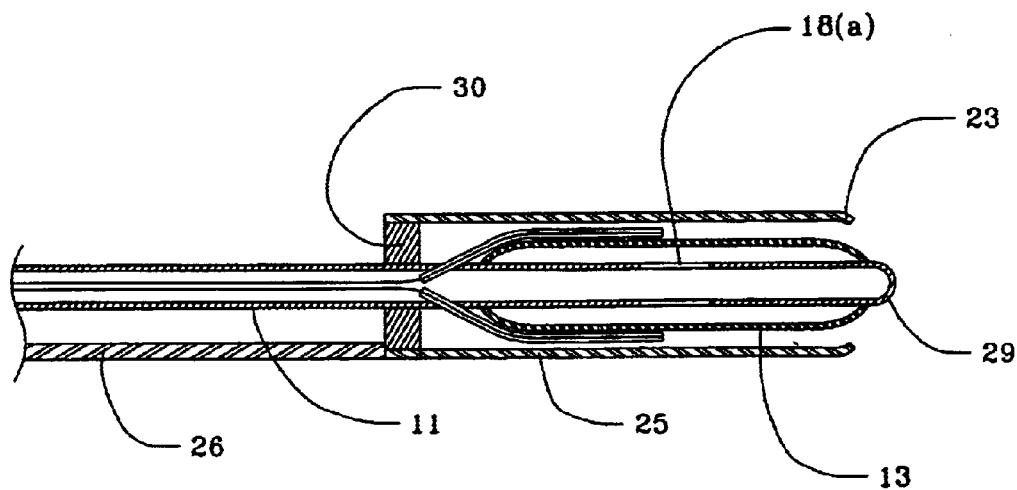
FIG. 6 is a partial, expanded, cross sectional, side view of a less preferred embodiment of the assembly of FIG. 5, in which the distal ends of the tubes are fully affixed to the balloon.

FIG. 6 illustrates the catheter/balloon/tube assembly of FIG. 1(b), with balloon 13 deflated, and disposed within movable outer sheath 25. The distal end of sheath 25 has an atraumatic, rounded, inwardly extending flange 29. Alternatively, the distal end of sheath 25 may be blunt ended (not shown) or may contain a rounded, outwardly extending flange (not shown). Gasket 30 is attached by an adhesive or other means inside the proximal end of sheath 25. Gasket 30 creates a friction fit with catheter 11 and centers catheter 11 within sheath 25. Gasket 30 also prevents sheath 25 from advancing beyond the point at which tubes 14 exit catheter 11.

In use, the distance the device is to be inserted into a body is measured by inserting a sound or other instrument, or by imaging, such as x-ray or ultrasound, or under direct vision through an endoscope. Catheter 11, with sheath 25 fully extended over balloon 13, is inserted the desired distance into the body, knowing the length of sheath 25 and noting the markings 27 on catheter 11. When properly positioned, a clamp may be attached to catheter 11 and the patient or the operating table, so the insertion distance is maintained. Knowing the length of balloon 13 (in this example 6 centimeters), sheath 22 may be retracted 6 centimeters by withdrawing flexible rod 26 until the proximal end of sheath 22 reaches the 6th centimeter mark 27 on catheter 11, fully exposing balloon 13. Then the balloon inflation, fiber insertion and lasing procedure may commence. When the lasing procedure has been completed, balloon 13 is deflated by removal of fluid, sheath 25 may be advanced by rod 26 to its original position, and catheter 11 and sheath 25 may be simultaneously removed. While rod 26 is shown here as a slender rod or bar, rod 26 may consist of several rods, a carved slat, or a slotted tube (not shown), which extends about 90° to 240° around the exterior of catheter 11, the slot enabling markings 27 on catheter 11 to be seen.

Figure 7:
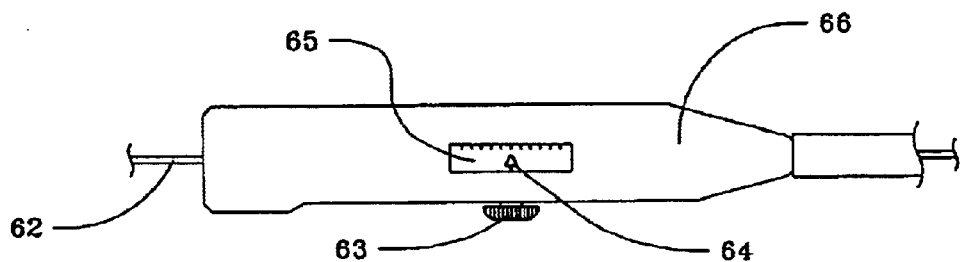
FIG. 7 is an external top view of an alternative embodiment of the handpiece of the device of FIG. 1.

As seen in FIG. 7, fiber bundle 62 may be advanced or retracted within handpiece 66 by advancing or withdrawing button 63, which is attached to fiber bundle 62 by an extension (not shown). Button 63 is disposed within a longitudinal slide (not shown) in handpiece 66. When button 63 is advanced or withdrawn, a ratchet mechanism (not shown) emits an audible "click". One audible "click" made by the ratchet mechanism can indicate fiber bundle 62 has been advanced a chosen distance, for example 1 mm. Optionally, a moveable arrow 64 in window 65 on the exterior surface of handpiece 66 can indicate the distance optical fiber bundle 62 has been advanced from the distal ends of the tubes 14 (not shown).

Figure 8A:
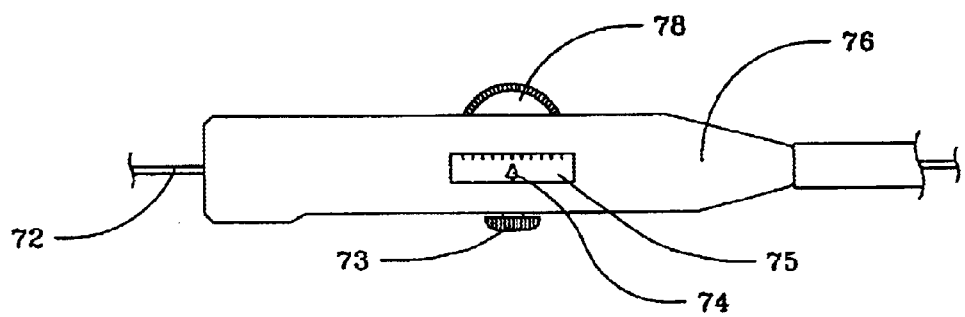
FIG. 8(a) is an external, top view of an alternate embodiment of the handpiece of the device of FIG. 1.
Figure 8B:
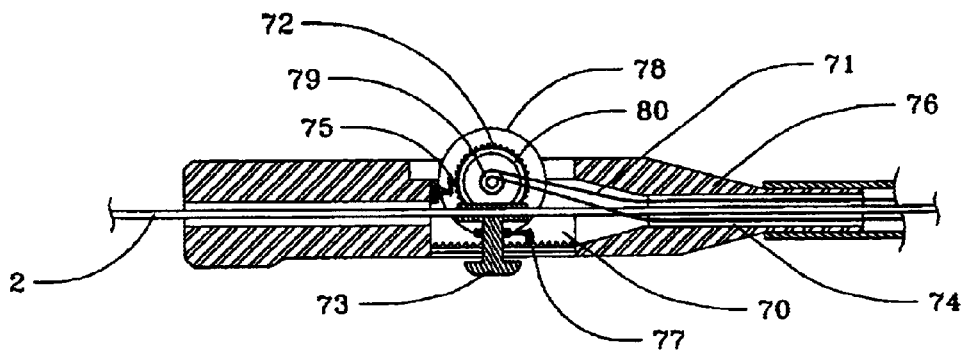
FIG. 8(b) is a partial, cross sectional top view of the handpiece of FIG. 8(a) with ratchet mechanism visible.

In another embodiment of the present invention, shown in FIG. 8(a) and FIG. 8(b), handpiece 76 contains button 73, arrow 74 and window 75, as described in FIG. 7, to advance and withdraw fiber bundle 72. Handpiece 76 also contains wheel 78, which is connected to shaft 79 within handpiece 76, as shown in cross-sectional view in FIG. 8(b).

Wheel 78 is fixedly attached to shaft 79, which extends perpendicular from the axis of wheel 78, and which is rotatably disposed within the body of handpiece 76. Flange 80 of wheel 78 has ridges 72 that engage ratchet mechanism 75, producing an audible click when wheel 78 has been rotated a predetermined amount, for example 5°. Knob 73 is slidably disposed in longitudinal slot 70 of handpiece 76, and ratchet mechanism 77 functions to emit an audible "click," as described in FIG. 7. The proximal ends of articulation wires 71, are attached to shaft 79. Articulation wires 71 extend through each of tubes 14, as described in the device of FIG. 5. When knob 78 is rotated, the proximal ends of articulation wires 71 are wound around shaft 79, retracting wires 71.

Figure 9:
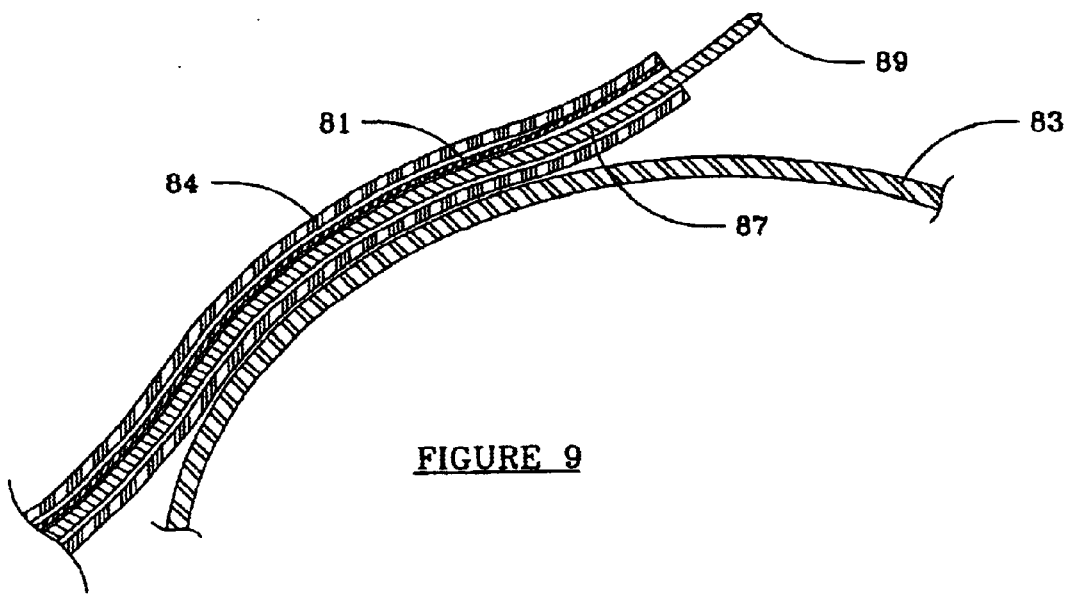
FIG. 9 is a partial, expanded, cross sectional side view of the inflated balloon of the device of FIG. 1, with the tubes and optical fibers manually articulated away from the balloon surface.

As shown in FIG. 9, the distal end of articulation wire 81 is attached to the inner surface of the distal end of tube 84, opposite the side of tube adjoining balloon 83, by adhesive or other means, as known in the art. Retracting articulation wire 81, as described in FIG. 8(b), causes tube 84, and optical fiber 87 contained therein, to be angled outward from balloon 83. Optionally, the distal end 89 of optical fiber 87 may be ground into a pointed shape, as shown, to enable optical fiber 87 to more easily penetrate tissue. A beveled or other shape may also be used. Articulation wire 81 may be made of nitinol or stainless steel, preferably with a diameter of about 0.005" to about 0.010". In FIG. 9, optical fiber 87 are shown in a position extended from tube 84. Articulation wires 81 are preferably retracted with optical fibers 87 fully retracted into tubes 84, e.g., prior to advancement of optical fibers 87 out of the distal ends of tubes 84.

Figure 10:
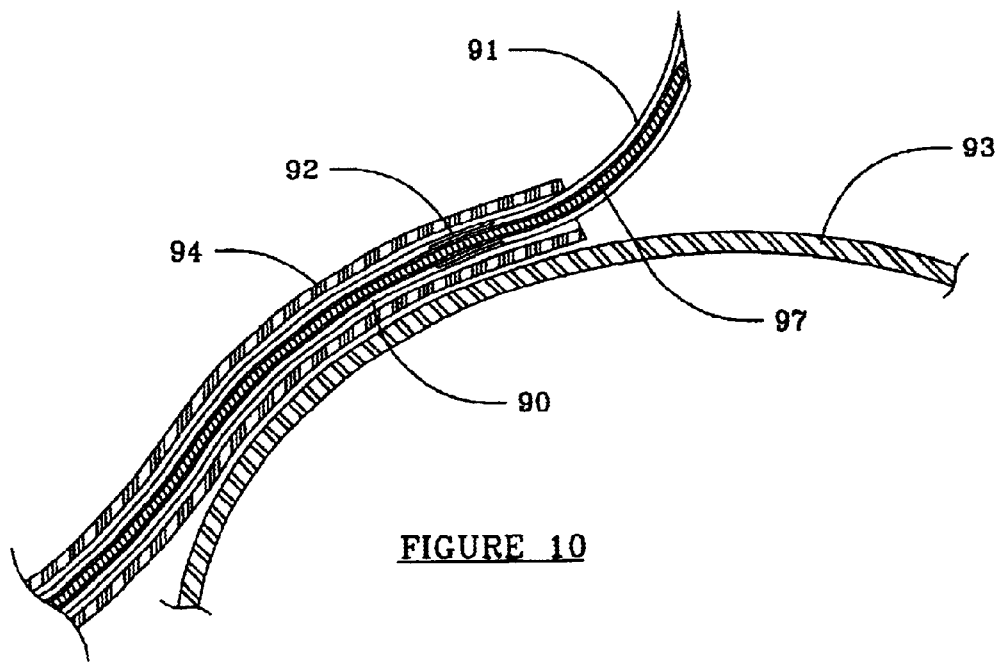
FIG. 10 is a partial, expanded cross sectional side view of the balloon/tube/fiber/wire assembly of an alternative embodiment of the device of FIG. 1.

As seen in FIG. 10, a partial, expanded view of a preferred embodiment of the present invention is shown. In this embodiment optical fiber 97 is sheathed within inner catheter 90, which is disposed within tube 94. The distal end of tube 94 is fully attached to the surface of balloon 93 as described in for the embodiment shown in FIG. 4. A syringe needle 91 is disposed over the distal end portion of optical fiber 97, and affixed thereto by crimping at two opposite points, for example, 3 and 9 o'clock, creating fluid passageways at 12 and 6 o'clock, as known in the art. Alternatively, the inner surface of syringe needle 91 may contain ridges or furrows, which provide a fluid passageway between the inner surface of syringe needle 91 and the exterior surface of optical fiber 97. The length of syringe needle 91 is preferably about 0.7 cm to about 6 cm, more preferably about 1 to about 4 cm. The distal end of inner catheter 90 is attached to the proximal end of syringe needle 91 by an adhesive or the like, creating a fluid passageway. Inner catheter 90 may overlap, and be attached by an adhesive or the like to the proximal end of syringe needle 91, or the proximal end of syringe needle 91 and the distal end of inner catheter 90 can each be shaped into complementary flanges, creating overlap 92 and thus producing a smooth, contiguous exterior surface.

In this particular embodiment, syringe needle 91 has a curved shape with a radius of curvature sufficient to create an angle of about 20° to about 100°, preferably about 40° to about 80° from the axis of optical fiber 97 when the syringe needle is partially extended a desired distance out from the distal end of tube 94. Syringe needle 91 is preferably composed of a superelastic shape memory alloy, most preferably a nickel—titanium (nitinol) alloy, such as TINEL™ available from Memry Corporation of Menlo Park, Calif. When confined within tube 94, the shape of syringe needle 91 conforms to the radius of curvature of the tube. However, when the syringe needle 91 is extended out of the distal end of tube 94, it resumes its prefabricated curved memory-shape. No external mechanical means is required to effect this change of shape. This property is referred to as shape memory. Syringe needle 91 is aligned within tube 94, so that when it is extended from its confinement within tube 94, syringe needle 91 resumes its curved shape and is angled outward from the surface of balloon 83, and thus penetrates the tissue surrounding the balloon 83. Optical fiber 87, may be extended outward from the distal end of syringe needle 91, if so desired.

A bulking material, such as a biocompatible collagen, for example Contigen™ distributed by C. R. Bard, Inc. of Murray Hill, N.J., or Zyplast™, an injectable collagen implant material made by Collagen Aesthetics, Inc. of Palo Alto, Calif., may be injected through the fluid passageways described in FIG. 10 into the tissue surrounding the esophagus to further reduce the diameter of the inner surface of the esophagus in the area of the sphincter by expanding the surrounding tissue. When collagen is heated to a temperature above 55° C., the collagen coils unwind into long tendrils. When collagen cools, the tendrils intertwine as they resume their coil forms. Such intertwining or mechanical cross-linking of the collagen reduces its propensity to migrate away from the injection site.

The collagen may be injected while laser or other thermal energy is being emitted, which heats the collagen and causes the aforementioned mechanical cross-linking of the collagen. Alternatively, the collagen may be injected first, and laser or other thermal energy may then be emitted to mechanically cross-link the collagen to keep it in place. Injection of a bulking material, can also be employed in other tissues as described herein. Thus, both shrinkage of the tissue from emission of laser energy and further reduction of the inner diameter of a duct, cavity, hollow organ or passageway in tissue can be achieved by injecting a bulking agent using the same device and avoiding a separate procedure.

Figure 11A:
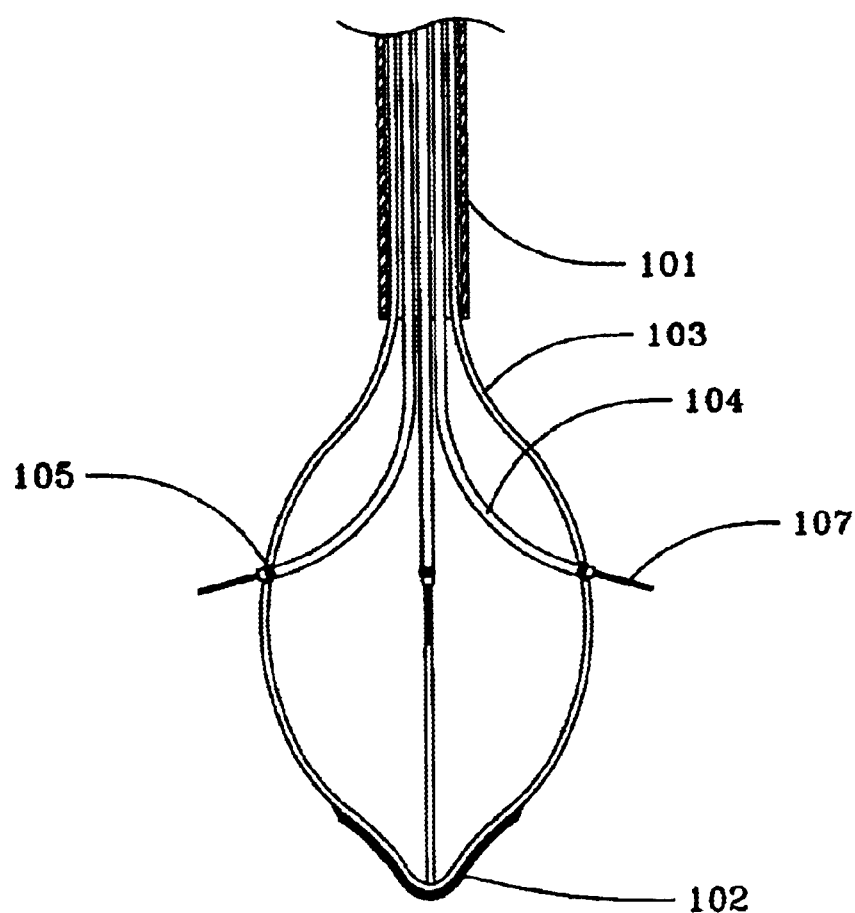
FIG. 11(a) is a partial, cross-sectional view of the distal end of an alternate embodiment of the device of the present invention.
Figure 11B:
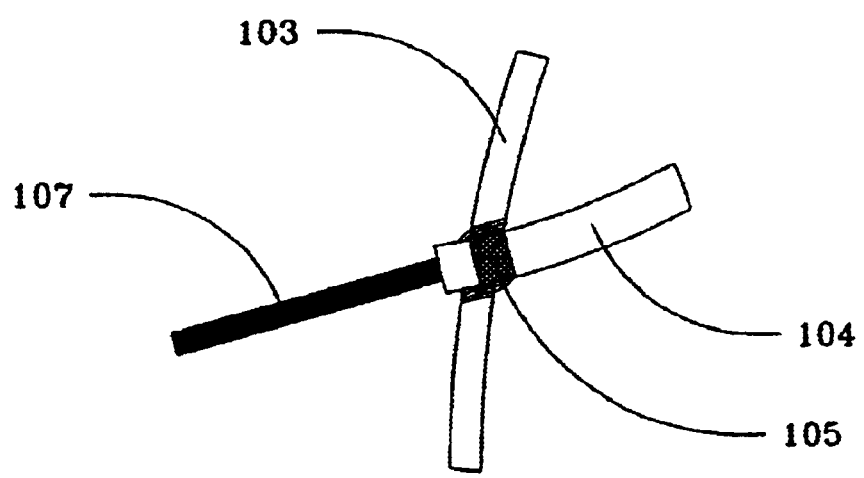
FIG. 11(b) is a partial, external view of a component of the device of FIG. 11(a).

FIGS. 11(a) and 11(b) depict an alternative embodiment of the present invention. In FIG. 11(a) the inflatable balloon of the previously described embodiments is replaced by a flexible cage comprising a plurality of flexible wires 103. Wires 103 are cylindrically disposed within catheter 101, throughout its whole length. The distal ends of wires 103 are attached to blunt shaped atraumatic cap 102 to form a cage structure. A plurality of tubes 104 are attached at their distal ends to wires 103 by flexible mesh bands 105. Mesh bands 105 are preferably made of a superelastic shape memory alloy such as nitinol. FIG. 11(b) shows an expanded view of the attachment point of tube 104 to wire 103. The whole cage structure may be retracted into or advanced out of catheter 101 as desired. In FIG. 11(a) the cage is shown advanced out of the distal end of catheter 101.

Tubes 104 extend throughout the entire length of catheter 101 and surround optical fibers 107. Optical fibers 107 are adapted at their proximal ends for connection to a source of laser energy, and may be retracted into or further extended from the ends of tubes 104, if the operator so desires. Tubes 104 are flexible and may be slidably moved within catheter 101, independent of the movement of wires 103. With the cage structure advanced out of the distal end of catheter 101, as shown, when the proximal ends of wires 103 are held stationary with respect to catheter 101, advancement of tubes 104 toward the distal end of catheter 101 causes flexible wires 104 to bow outward to form an expanded cage. Flexible mesh bands 105 then cause the distal ends of tubes 103 to point outward, away from the axis of the catheter 101. Optical fibers 107 may then be extended out of the distal end of tubes 103 into the surrounding tissue. Laser energy or other thermal energy may then be applied to the surrounding tissue as described for the other embodiments.

In an alternative embodiment, not shown in the FIGURES, each of optical fibers 107 may be enclosed within an inner catheter and may have a short length of syringe needle affixed to their distal ends, as described in FIG. 10. The resulting fluid passageway may be used to inject a bulking material, such as collagen, as described above.

In another alternate embodiment, not shown, the cage structure comprising wires 103 and attached tubes 104, in which optical fibers 107 are slidably retained, may be disposed, if desired, within the retractable protective sheath 25 described in FIGS. 1(b), 1(c), 1(d) and 6 herein, to facilitate atraumatic insertion of the wire/tube/fiber assembly into a hollow organ, cavity, duct or passageway.

Lasers which may be utilized with the above described devices include, without limitation argon, KTP, diode, Nd:YAG, Alexandrite and Holmium:YAG, the latter requiring optical fibers with a low OH content. High intensity white light may also be used.

At a given position in the esophagus, after the optical fibers have been deployed, an argon, KTP, diode, Nd:YAG, Alexandrite or other laser may be used at an energy level of about 5 to 30 watts for about 5 seconds to 1 minute, after which the device can be repositioned and the procedure repeated until a sufficient shrinkage or tightening of the tissue around the esophagus has occurred. If a Holmium:YAG laser is being used, about 0.2 to 1 joule per pulse of laser energy at a repetition rate of about 3 to 30 hertz may be employed for about 5 seconds to 1 minute. In the female urethra, for example, less energy for a shorter period of time will be sufficient to achieve the desired shrinkage effect, due to the smaller size of the duct and surrounding tissue.

The above described devices may be made of various elastic, flexible or rigid materials and in various sizes, depending upon the application. For use through the mouth into the esophagus, the outside diameter of sheath 25 of the device of FIG. 1(c) can be 4 mm to 15 mm in diameter, preferably about 6 to 10 mm. For use in the female urethra, the outside diameter of sheath 25 should be much smaller, preferably about 2 to 6 mm in diameter.

Numerous variations and modifications of the embodiments described above may be effected without departing from the spirit and scope of the novel features of the invention. It is to be understood that no limitation with respect to the specific apparatus illustrated herein is intended or should be inferred. It is, of course, intended to cover by the appended claims all such modifications as fall within the scope of the claims.

We claim:

1. A medical device suitable for shrinking collagen and scarring tissue comprising:
   a catheter having a distal end, a proximal end, an internal lumen having a corresponding distal end and a corresponding proximal end, and a plurality of openings proximal to the distal end of the catheter;
   an elongated inflatable balloon at the distal end of the catheter and having an outer surface;
   a plurality of hollow tubes each with a proximal end portion and a distal end portion, the proximal end portion of each tube in communication with the distal end of the catheter and extending longitudinally along the external surface of the balloon and terminating before the distal end of the balloon exterior;
   a plurality of optical fibers, extending through the lumen and into said hollow tubes, each optical fiber having a proximal end adapted for connection to a source of coherent light and a distal end, the optical fibers being slidably moveable along the lumen and along the tubes, between a protruding position beyond the distal ends of the tubes and a position inside the tubes; and
   a handpiece at the proximal end of the catheter, the handpiece being operably attached to the optical fibers for controlling movement of the optical fibers through the lumen and tubes; and
   wherein the catheter further includes:
      an open cylindrical protective sheath, moveably disposed over the inflatable balloon; and a flexible rod, attached to the distal end of the protective sheath, for retracting and advancing the sheath to expose and cover the balloon.

2. The medical device of claim 1, wherein the optical fibers are surrounded by a casing, and are slidably moveable in the casing.

3. The medical device of claim 1, wherein the catheter is provided with a rounded distal end portion.

4. The medical device of claim 1, wherein the distal end of the catheter defines one or more ports for transfer of an inflation medium between the lumen and the balloon.

5. The medical device of claim 1, further comprising a plurality of articulation wires, each having a distal end and a proximal end, said wires extending through the entire length of the lumen and through each tube, the distal end of each wire being affixed to the distal end of the tube through which it extends, and wherein the handpiece is operably attached to the proximal ends of the articulation wires for controlling the movement of the articulation wires; such that when the articulation wires are retracted, the distal ends of the tube are turned outward, away from the outer surface of the balloon.

6. The medical device of claim 4 further comprising a hollow fluid tube for transferring the inflation medium between the fluid tube and the lumen, the fluid tube having a distal end and a proximal end, and with the distal end of the fluid tube connected to the lumen, and the proximal end of the fluid tube attached to a source of inflation medium.

7. The medical device of claim 6, wherein the fluid tube is provided with a luer lock connector at the proximal end thereof.

8. The medical device of claim 1, wherein the distal end portions of the optical fibers are encased in a flexible curved syringe needle having a sharp distal end, the curvature of the needle oriented such that the distal end of the needle points away from the outer surface of the balloon when the optical fibers are advanced distally through the tubes; and wherein the syringe needle is composed of a superelastic shape memory alloy, so that when the optical fibers and needle are retracted into the tubes, the radius of curvature of the needle increases and the needle conforms to the shape of the tube.

9. The medical device of claim 8, wherein the handpiece is operably attached to the proximal ends of the optical fibers for controlling movement of the optical fibers through the lumen and tubes.

* * * * *